United States Patent [19]

Johnson et al.

[11] 3,994,931

[45] Nov. 30, 1976

[54] PURIFICATION AND HYDROGENATION OF FURAN CONCENTRATES

[75] Inventors: Marvin M. Johnson; Donald C. Tabler, both of Bartlesville, Okla.

[73] Assignee: Phillips Petroleum Company, Bartlesville, Okla.

[22] Filed: Feb. 7, 1975

[21] Appl. No.: 547,941

Related U.S. Application Data

[60] Division of Ser. No. 286,728, Sept. 6, 1972, Pat. No. 3,883,566, which is a continuation-in-part of Ser. No. 175,432, Aug. 27, 1971, abandoned.

[52] U.S. Cl. .......................................... 260/346.1 R
[51] Int. Cl.² ...................................... C07D 307/02
[58] Field of Search .......... 260/346.1, 683.9, 680 E, 260/346.1 R; 252/472, 80

[56] References Cited

UNITED STATES PATENTS

| | | | |
|---|---|---|---|
| 2,479,306 | 8/1949 | Cairns | 260/88.1 |
| 3,629,149 | 12/1971 | Mulaskey | 252/439 |
| 3,639,521 | 2/1972 | Hsieth | 260/880 |
| 3,642,658 | 2/1972 | Allum et al. | 252/472 |
| 3,864,363 | 2/1975 | Kile | 260/346.1 |

OTHER PUBLICATIONS

Kirk–Othmer, Encyclopedia of Chemical Technology, 2nd ed., vol. 10, pp. 237–250 (Interscience Publishers, Inc.).

Kice et al., Modern Principles of Organic Chemistry, p. 355, The Macmillan Co., NY.

*Primary Examiner*—John D. Randolph

[57] ABSTRACT

Furan concentrates containing deleterious unsaturated contaminants including sulfur compounds are purified prior to hydrogenation by contacting with zinc oxide either prior to or subsequent to separation of high boiling materials from the concentrate with the result that the furan concentrate is hydrogenated to high purity product comprising either furan and saturated materials or tetrahydrofuran and saturated materials with extended hydrogenation catalyst life. In a preferred embodiment, the furan concentrate is obtained as the by-product stream from hydrocarbon oxidative dehydrogenation processes and is subjected to distillation to remove therefrom materials boiling above about 80° C prior to contacting with zinc oxide and hydrogenation.

11 Claims, 1 Drawing Figure

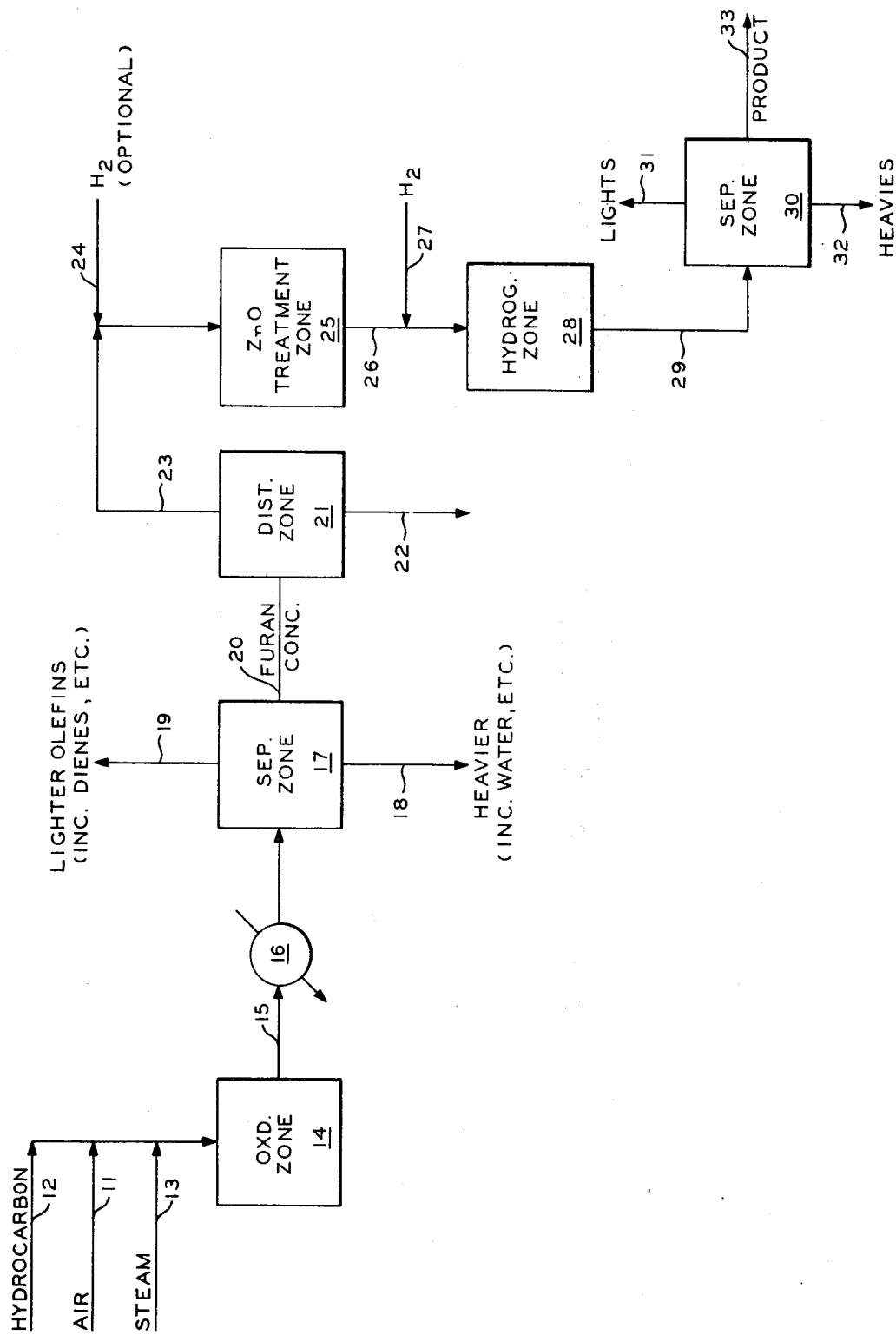

PURIFICATION AND HYDROGENATION OF FURAN CONCENTRATES

This is a divisional application of Ser. No. 286,728, filed Sept. 6, 1972, now U.S. Pat. No. 3,883,566, which in turn is a continuation-in-part application of our co-pending application having Ser. No. 175,432, filed Aug. 27, 1971, entitled "Purification and Hydrogenation of Furan Concentrates", now abandoned.

This invention relates to the purification and hydrogenation of streams containing furan. In accordance with another aspect, this invention relates to the purification and hydrogenation of a furan concentrate obtained as part of an effluent from an oxidative dehydrogenation process. In accordance with another aspect, this invention relates to rendering deleterious contaminants including sulfur compounds present in furan concentrates innocuous by contacting with zinc oxide prior to hydrogenation of the furan. In accordance with a further aspect, this invention relates to the purification of furan concentrates containing catalyst inactivating materials by separating therefrom materials boiling above about 80° C either prior to or subsequent to zinc oxide contacting of the furan concentrate, prior to hydrogenation. In accordance with another aspect, this invention relates to the oxidative dehydrogenation of hydrocarbons followed by the recovery of a furan concentrate from the effluent which concentrate is purified prior to hydrogenation to tetrahydrofuran by a combination of distillation and zinc oxide treatment. In accordance with a further aspect, it has been found that unsaturated materials such as olefins, acetylenes, and diolefins can be selectively hydrogenated in the presence of unsaturated ethers. In accordance with still another aspect, this invention relates to a process for hydrogenating furan concentrates to high purity products comprising either furan and saturated materials or tetrahydrofuran and saturated materials.

In a recent butene dehydrogenation process known as oxidative dehydrogenation, an oxygen-containing gas is fed to the catalytic reaction zone containing a catalyst such as stannic phosphate along with the butene feed and steam, and a substantial portion of the hydrogen produced by dehydrogenation is combusted to water vapor. This not only removes the inhibiting effect of the hydrogen on further dehydrogenation, but also supplies heat to this endothermic reaction, resulting in high conversions and per-pass yield of butadiene at relatively good selectivity. By this method, additional steam is produced which is recovered from the process effluent as condensate. Also, moderate concentrations of oxygenated hydrocarbons are generated which similarly appear in the condensed steam and/or in the hydrocarbon effluent.

A highly reactive dehydrogenation catalyst comprising tin phosphate has recently been disclosed and claimed by Nolan in U.S. Pat. No. 3,320,329. As is set forth in that patent, compounds to be dehydrogenated, preferably selected from the group consisting of alkenes, cycloalkenes, alkylpyridines, and alkyl aromatics, are mixed with oxygen or an oxygen-containing gas, preheated, and passed over a catalyst comprising stannic phosphate at a temperature in the range of 700° to 1300° F. Generally, the inlet temperature of the gas is around 800° to 900° F.

The oxygen used in the dehydrogenation is present in an excess in order to insure complete conversion of hydrogen released in the dehydrogenation reaction. Therefore, the effluent from the dehydrogenation reaction will contain unreacted oxygen gas as well as a number of oxygenated products of the reaction. This residual oxygen and the oxygenated compounds are corrosive and are subject to polymerization and are, therefore, detrimental to the further processing of the hydrocarbon product. It is, therefore, necessary that the oxygen and oxygen-containing compounds be removed from the effluent streams.

It has been found that a small percentage of the olefin feed is converted to oxygenated hydrocarbons such as furans, alcohols, acids, aldehydes, ketones, etc., the nature and quantity of these compounds depending upon the conditions under which the dehydrogenation is effected. Under normal plant operating conditions, these oxygenated by-products will be ultimately fed into the atmosphere and/or discharged with waste water and/or end up in a heavy hydrocarbon-containing fraction, depending upon the separation and recovery processes employed and their operating conditions.

The present invention is directed to the purification of furan concentrates containing catalyst inactivating materials and subsequently hydrogenating the purified furan concentrate to produce high purity products comprising either furan and saturated materials or tetrahydrofuran and saturated materials.

It has been found that not all furan concentrates can be hydrogenated with equal ease and that in some instances the life of the hydrogenation catalyst is relatively short. Since hydrogenation catalysts are ordinarily quite expensive, e.g., nickel catalysts, and ordinarily not readily regenerable, short catalyst life is an important economic consideration in the production of tetrahydrofuran.

It has now been found that the cause of the problem is the somewhat unexpected presence of sulfur compounds in the furan concentrates. The source of the sulfur compound contamination is not known with certainty, but it is presently surmised that the water, of which copious quantities are used in the oxidative dehydrogenation process, is possibly the source because of the sulfite or sulfate compounds it may contain either naturally or from prior water treatment processes.

Irrespective of where the sulfur comes from, we have identified the problem and have now provided an effective and novel solution to the problem of poor or erratic hydrogenation of furan concentrate.

In accordance with the invention, it has now been found that the nature of the furan concentrate is such that it requires, to be readily hydrogenatable, both a separation to a selected end point and a high temperature treatment in contact with zinc oxide.

Accordingly, an object of this invention is to provide an improved process for the hydrogenation of furan concentrate.

Another object of this invention is to provide a process for the removal of deleterious contaminates including sulfur compounds from furan concentrates prior to hydrogenation.

A further object of this invention is to provide a process for the purification of furan concentrates to improve the hydrogenatability of the concentrates.

Other objects and aspects, as well as the several advantages of the invention, will be apparent to those skilled in the art upon reading the specification, the drawing, and the appended claims.

In accordance with the invention, the hydrogenatability of furan concentrates containing deleterious contaminates including sulfur compounds is improved by subjecting the concentrate to a high temperature treatment in contact with zinc oxide.

In accordance with one embodiment of the invention, a furan concentrate is separated into a high boiling and a low boiling fraction, and the low boiling fraction contacted with zinc oxide prior to hydrogenation to convert furan to tetrahydrofuran.

In accordance with another embodiment of the invention, it has been found that unsaturated materials such as acetylenes, olefns, and diolefins can be selectively hydrogenated to saturated materials in the presence of unsaturated ethers such as furan by contacting with selected catalysts under hydrogenation conditions.

In accordance with another embodiment of the invention, furan concentrates containing unsaturated materials such as olefins, acetylenes and diolefins, as well as sulfur compounds, are hydrogenated to high purity products comprising either furan and saturated materials or tetrahydrofuran and saturated materials, the hydrogenation being carried out in the presence of selected hydrogenation catalysts under hydrogenation conditions.

In accordance with carrying out the hydrogenation using a catalyst and reaction conditions which are milder and more selective to selectively hydrogenate unsaturated materials in the presence of furan, for example, the furan concentrate is selectively hydrogenated such that the more readily hydrogenatable olefins, diolefins, alkynes, and the like are hydrogenated, but the furan is affected but little, if at all. A product of this hydrogenation thus would be a furan concentrate in which the furan is diluted with hydrocarbons which are essentially parafinic. Although the paraffin-diluted furan mixture is not readily separable by fractionation, there are applications where this furan mixture can be used without prior removal of the paraffins such as being used for a polymerization feed.

In accordance with a specific embodiment, furan concentrates containing hydrogenation catalyst inactivating materials are purified prior to hydrogenation by subjecting the furan concentrate first to distillation to remove therefrom materials boiling above about 80° C, followed by contacting at high temperature with zinc oxide.

Further in accordance with the invention, the effectiveness of the zinc oxide absorbent used in desulfurizing the furan concentrate prior to hydrogenating furan concentrate is improved and the capacity of the bed to hold the sulfur is increased by impregnating the zinc oxide with a base, for example, an inorganic base such as sodium hydroxide, sodium carbonate, sodium zincate, and the like.

In accordance with another embodiment of the invention, the furan concentrate is first contacted at high temperature with zinc oxide and then subjected to distillation to remove therefrom materials boiling above about 80° C prior to hydrogenation of the concentrate.

In accordance with a further specific embodiment of the invention, a furan concentrate is obtained as a portion of the effluent from a butenes oxidative dehydrogenation, which concentrate is subjected to distillation to a selected end point and a high temperature treatment in contact with zinc oxide prior to hydrogenation.

The furan concentrate, hereinafter called the first furan concentrate, which is applicable for the treating and hydrogenation sequence of the present invention is a substantially water-insoluble furan-containing fraction of the by-products formed from an oxidative dehydrogenation process wherein a hydrocarbon is converted to at least one less saturated product. The specific hydrocarbon feed or the specific catalyst of the oxidative dehydrogenation is not critical. Preferably, however, the feed is a $C_4$ hydrocarbon, particularly normal butenes. The oxidative dehydrogenation of butenes to butadiene can be carried out in the presence of a number of catalysts including a tin phosphate catalyst as disclosed and claimed by Nolan in U.S. Pat. No. 3,320,329, as well as in the presence of other catalysts such as calcined catalytic composition prepared from a phosphorus-containing material, such as phosphoric acid, a tin material such as tin cloride, and one of a Group IA or IIA metal or metal-containing material as disclosed and claimed by Nolan et al in U.S. Pat. No. 3,789,078. The by-product furan fraction can be narrow or broad in boiling range, but should contain a significant amount of furan, say, at least five weight percent. Preferably, it should be relatively free of ligher boiling materials such as butenes and butadiene, but this is an economic rather than a technical preference.

In practice, the first furan concentrate can be obtained by consecutively subjecting the oxidative dehydrogenation reactor effluent to removal of water and water-solubles such as by an aqueous quenching step, removal of light gases such as by an absorption-stripping step, and removal of principal dehydrogenation products by a fractionation step. The remaining furan-containing fraction is then subjected to the process combination of the present invention.

Because the furan concentrate is a broad boiling range material and apparently contains some heavier sulfur-containing materials which do not readily respond to the zinc oxide treatment, it is necessary that the first furan concentrate be distilled to provide a second concentrate such that the end point of the second concentrate is less than the boiling point of thiophene, that is, less than about 84° C (183.2° F) at 760 mm Hg. Preferably, the end point of the distillate should be no more than about 80° C (176.0° F). Thus, the distillation should be carried out so as to provide a furan-containing distillate which is significantly free of materials boiling above about 80° C (176° F).

The boiling point of furan is about 32° C (89.6° F). However, because the complex mixture of the furan concentrates is capable of producing azeotropic mixtures, the effective boiling point of mixtures containing substantial amounts of furan can be as low as 28° C (82.4° F), or even lower. The presence of materials boiling below furan is not critical. Hence, this second furan concentrate can have any convenient initial boiling point (IBP).

In batch distillations, the second concentrate will generally contain a substantial amount of material boiling within the range of 28° C (82.4° F) to 80° C (176° F), preferably 28° C (82.4° F) to 60° C (140° F), still more preferably 28° C (82.4° F) to 50° C (122° F). In continuous operations, a continuously operating fractionating column will have its head temperature within one of these aforesaid ranges to produce a suitable second concentrate.

The zinc oxide treatment of the present invention comprises contact of the suitable furan concentrate with the zinc oxide at temperatures in the range of from about 550° to about 850° F and at any convenient pressure such as, for example, atmospheric to about 250 psig. The contact is carried out in the vapor phase and at rates which will vary with the nature of the specific furan concentrate being treated. Ordinarily, the rates will be in the range of from about 0.1 to about 10, preferably 1–5, LHSV. In general, the treatment will be sufficient to substantially reduce the total sulfur content of the furan concentrate.

Optionally, hydrogen can be present in the zinc oxide treatment zone in amounts ranging from trace amounts to those concentrations utilized in the subsequent furan hydrogenation stage.

The zinc oxide contactor ordinarily uses any suitable zinc oxide, either natural or synthetic, having a zinc oxide content greater than about 10 weight percent, and preferably greater than about 50 weight percent, with the remainder being an inert binder such as a silicon-containing material. Other inert materials can be employed, if desired. Any convenient mode of contacting can be used although fixed bed operation is presently preferred.

As indicated above, the effectiveness of the zinc oxide absorbent can be improved by treatment of the zinc oxide with a base such as sodium hydroxide, sodium carbonate, sodium zincate, and the like prior to contacting with the furan concentrate. The amount of base added can be in the range of one to ten weight percent. Other basic materials that can be employed include alkaline earth hydroxides such as calcium hydroxide and the other alkali metal carbonates, hydroxides, and zincates such as the potassium derivatives.

Although the desulfurized second furan concentrate which is to be hydrogenated can be prepared for efficient hydrogenation by first undergoing the zinc oxide treatment and then the distillation, the reverse order of these treatments is presently preferred. That is, it is generally more convenient to subject the furan concentrate to the required distillation and then to carry out the zinc oxide treatment on the distillate. It has been found that the broad mixture of materials which comprise the furan concentrate contains at least minor amounts of readily polymerizable materials such as styrene. Hence, it is generally more convenient to first carry out the distillation because this operation separates the heavier styrene from the lighter fraction which contains the bulk of the furan. Operation in this manner minimizes the opportunity for polymerizables such as styrene to form polymers within the zinc oxide treater.

In accordance with one embodiment of the invention, the pretreated concentrate is hydrogenated using any suitable process and catalyst which is capable of converting the furan to maximum amounts of tetrahydrofuran with minimum amounts of n-butanol by-product. Nickel-containing catalysts, such as Raney nickel, are particularly useful. Hydrogenation conditions can include 100°–400° F in temperature and 0–1000 psig.

In accordance with another embodiment of the invention, if hydrogenation of the furan concentrate to an improved furan concentrate is desired, selective hydrogenation catalysts and conditions are used which are sufficient to convert olefins, diolefins, alkynes, and the like to the corresponding paraffins but are insufficient to convert significant amounts of the furan to tetrahydrofuran. Any catalyst system which has this desired degree of selectivity and any reaction conditions which have the desired degree of severity can be used to carry out this selective hydrogenation. A particularly appropriate group of catalysts can be represented by the empirical formula $MeAs_x$ wherein Me represents nickel, cobalt, or iron, and $x$ is a number which corresponds to the amount of arsenic required to sufficiently modify the metal catalyst to provide desired degree of selectivity. Nickel is preferred, and $x$ is preferably in the range of 0.1–0.5.

The metal arsenide is preferably supported on a conventional catalytic support material such as alumina, magnesia, charcoal, calcium aluminate, and the like. The support-containing catalyst will contain from about 0.1 to about 20, preferably 2—15, weight percent of the Me metal.

Such catalysts can be prepared by any suitable method. Conventional methods such as coprecipitation, impregnation, dry-mixing, wet-mixing, and combinations thereof can be used. Impregnation methods are presently preferred, and the suitable support material can be conventionally impregnated with inorganic compounds including salts such as the nitrates, halides, and the like of the metal components. Similarly, aqueous aresenic acid, or arsenic trioxide in an ammoniacal solution, can be employed as impregnates.

Whichever method of catalyst preparation is used, the catalyst composite should be washed free of non-volatiles, dried, then calcined at elevated temperatures in air. Finally, the catalyst is reduced with hydrogen at any suitable temperature and for any suitable time which is sufficient to produce the active catalyst. For example, the hydrogen reduction can be carried out at 500°–1100° F for 0.1–20 hours. In some instances, the calcination in air step can be omitted. Catalyst regeneration, when this is necessary, can follow a similar sequence of calcination and reduction.

When it is desired to produce a paraffin-diluted furan concentrate, the furan-containing material is brought into contact with a suitable catalyst together with hydrogen at temperatures in the range of about 75°–750° F, preferably 150°–500° F. Any convenient pressure can be used such as from 0 to about 1000 psig. The process is preferably carried out continuously and at temperatures and feed rates which are sufficient to provide the level of hydrogenation severity to bring about the desired result. Feed rates will generally be in the range of 0.1–10 LHSV. The hydrogen will be present in the reaction zone to provide a molar ratio of hydrogen to feed of from about 0.1:1 to about 5:1.

A better understanding of the invention will be obtained upon reference to the accompanying drawing which illustrates one embodiment of the invention in combination with the processing following butenes oxidative dehydrogenation.

Referring now to the drawing, air by line 11, hydrocarbon feed by line 12, and steam by line 13 are introduced into oxidative dehydrogenation (OXD) reactor 14. The conditions for carrying out oxidative dehydrogenation are set forth above and are described in detail in U.S. Pat. No. 3,320,329.

An oxidative dehydrogenation effluent, for example, a butenes oxidative dehydrogenation effluent comprising butenes, butadiene, isoprene. butyne-2, piperylenes, pentenes, etc., and oxygenated hydrocarbons including furan, steam, oxygen, and other materials, is removed from oxidative dehydrogenation reactor 14 by way of line 15, passed through cooler 16 wherein the effluent is cooled from the reactor temperature to the order of about 240° F before passage to separation zone 17. It should be understood that a number of coolers can be provided to cool the oxidative dehydrogenation effluent to a suitable temperature for processing in separation zone 17. An aqueous phase, heavier hydrocarbons, and heavier oxygenated hydrocarbons contained in the reactor effluent are removed from separation zone 17 by way of line 18. Unreacted hydrocarbons, dehydrogenated hydrocarbon product, e.g., butadiene, and lighter materials contained in the effluent removed from reactor 14 are taken overhead from separation zone 17 by way of line 19. Separation zone 17 can comprise a number of fractionators or a combination of fractionators and absorber-stripper units.

A first furan concentrate is removed from separation zone 17 by way of line 20 and passed to distillation zone 21 wherein the concentrate is subjected to distillation conditions so as to remove as bottoms materials, including some sulfur compounds as thiophene, in the concentrate boiling above about 80° C. The heavier materials are removed from distillation zone by way of line 22 to provide a second furan concentrate as an overhead distillate in line 23. This second furan concentrate in line 23 can be mixed with hydrogen if desired, by line 24, heated (not shown), and passed through treatment zone 25 containing zinc oxide. The feed to treating zone 25 is a mixture of furan and a number of close-boiling olefins, diolefins, paraffins, alkynes, and still contains catalyst-inactivating materials which are rendered innocuous by contact with zinc oxide in zone 25.

The second furan concentrate, now substantially freed of catalyst inactivating materials, is removed from zone 25 by way of line 26, cooled (not shown), mixed with additional hydrogen, if necessary, by way of line 27, and introduced into hydrogenation zone 28 wherein the furan is substantially converted to tetrahydrofuran (THF) depending upon the hydrogenation conditions and catalyst as disclosed above. If desired, the hydrogenation conditions and catalyst can be so chosen as to hydrogenate substantially only the olefinic, acetylenic, and diolefinic materials without hydrogenating the furan, and the effluent produced would comprise furan and saturated hydrocarbon materials. The effluent is removed from hydrogenation zone by way of line 29, cooled (not shown), and passed to separation zone 30 wherein light materials are taken overhead by way of line 31 and heavier materials by way of line 32. Separation zone 30 can comprise two or more fractionators or other separation means. In one embodiment, a high purity tetrahydrofuran product is now removed by way of line 33 because its boiling point, about 151° F, is now substantially different from other members of the mixture. In another embodiment, a furan concentrate comprising furan and saturated hydrocarbon materials is removed as a high purity product and can be used as such without prior removal of the paraffinic hydrocarbons as a polymerization feed.

The hydrogen introduced by either line 24 or line 27 can be added in the form of pure hydrogen, a hydrogen gas diluted with an inert diluent such as nitrogen, or any other hydrogen-containing gas. Reaction of hydrogen with the oxygen-containing materials and especially furan in zone 28 occurs at a temperature of from about 100° to about 400° F, preferably from about 200° to about 300° F, and a pressure of from about 0 to about 1000 psig, preferably about 100 to about 300 psig. The temperature, of course, depends on the type of catalyst employed. If it is desired to produce a paraffin-diluted furan concentrate, the furan-containing material is brought into contact with a metal arsenide catalyst, as defined above, with hydrogen under suitable hydrogenation conditions, as defined above.

The hydrogenation of furan to tetrahydrofuran can be conducted with metal catalyts such as cobalt, nickel, and ruthenium with suitable supporting or diluting materials such as alumina, carbon, silica, or other similar materials. As indicated previously, the hydrogenation of unsaturated hydrocarbon materials present in the furan concentrate without any substantial amount of hydrogenation of the furan can be carried out in the presence of metal arsenide catalyts as defined above.

Although not shown in the drawing, the hydrogenation effluent which comprises principally hydrogen, tetrahydrofuran, and paraffinic hydrocarbons such as butane and isopentane is removed from hydrogenation zone 28 and can be cooled by an exchanger (not shown) and passed to a phase separator (not shown) prior to passing the effluent to other separation units of separation zone 30. Uncondensed materials, including hydrogen removed from the hydrogenation effluent, are separated in the phase separator and can be returned to the hydrogenation reactor as recycle (not shown). Product liquid which comprises tetrahydrofuran, isopentane, and butane and a small amount of hydrogen and other materials can be passed in toto to other separation units of separation zone 30 or a portion of it can be recycled as feed to the hydrogenation zone for temperature control. In another embodiment, the hydrogenation effluent comprising hydrogen, furan, and paraffinic hydrocarbons can be subjected to further separation or treatment as desired in a manner similar to that defined above for the recovery of tetrahydrofuran product.

EXAMPLE I

In this example of an invention run, a quantity of a first furan concentrate, obtained as a by-product from an oxidative dehydrogenation reaction in which butene-2 was converted to butadiene, was sequentially contacted with zinc oxide at elevated temperatures, distilled, then the overhead distillate was subjected to hydrogenation in the presence of Raney nickel to produce tetrahydrofuran.

The first furan concentrate, obtained from the oxidative dehydrogenation process, was broad mixture and chemical analysis showed the following materials to be present:

| Component | Weight Percent |
| --- | --- |
| Furan | 49.62 |
| Methacrolein | 8.66 |
| Vinylcyclohexene | 5.79 |
| Benzene | 5.96 |
| Toluene | 2.05 |
| Others | 27.92 |
| Total Sulfur | 190 ppm |

The above-described first furan concentrate was passed through a cylindrical reactor which was packed with about 65 of −10/+40 mesh zinc oxide at the rate of about 4 LHSV. The reactor was maintained at 570°–590° F and 120 psig. The reactor effluent was found to contain 59 ppm total sulfur.

About 300 cc of the above ZnO-treated furan concentrate was then charged into an autoclave together with about 1 gram of Raney nickel catalyst for hydrogenation at 270° F and at 500 psig. The hydrogenation was found to proceed very slowly. Consequently, the liquid was removed from the autoclave and distilled to a temperature of 37° C (98.6° F) and the overhead distillate was collected. The overhead distillate (140 cc) was found to have 3 ppm total sulfur. (About 10 cc liquid was lost in the operation.)

About 70 ml of the above distillate was diluted with 440 ml of n-pentane and mixed with Raney nickel, then subjected to hydrogenation at 500 psig at 260° F. The uptake of hydrogen was found to be very rapid, and, after about 7 hours, it was found that the furan had been completely converted to tetrahydrofuran except for traces of n-butyl alcohol.

The results of this run are shown in Table I as Run No.4. For purposes of comparison, the results of several other runs which utilized only the distillation or which utilized only the zinc oxide treatment are also shown. These are Runs 1, 2, and 3.

The data in Table I clearly show the benefits obtained when the furan concentrate, containing a relatively large quantity of sulfur compounds, is subjected to both a zinc oxide treatment and a distillation to remove high boiling materials. In those runs in which only the distillation was employed or which only the zinc oxide treatment was employed, the hydrogenation rate was found to be very slow. Hydrogenation (not shown in the table) of the furan concentrate which is neither distilled nor subjected to the zinc oxide treatment is even poorer than Runs 1–3.

EXAMPLE II

In this example of an invention run a different first furan concentrate, having a different level of sulfur compound contamination, was subjected first to a distillation and then to a zinc oxide treatment to render it easily hydrogenatable to tetrahydrofuran.

The first furan concentrate used in this run was similar to that described in Example I except that its total sulfur content was about 57 ppm. This concentrate was first distilled and an overhead fraction boiling at 81.5°–84° F was collected. This fraction was found to contain about 23 ppm total sulfur and had an analysis, in weight percent, as shown below.

| | |
|---|---|
| Isopentane | 4.44 |
| 1,3-Pentadienes | 1.77 |
| Furan | 88.04 |
| Others | 3.58 |
| Butyne-2 | 2.17 |

In a manner similar to that of Example I the distilled second furan concentrate was passed over zinc oxide at 550° F and at 200 psig. The effluent from the zinc oxide reactor was found to contain only 1 ppm total sulfur.

Also in a manner similar to that of Example I the above distilled and zinc oxide-treated material was subjected to hydrogenation in the presence of Raney nickel at 250° F and at 500 psig. The hydrogenation to tetrahydrofuran was very rapid and was essentially complete in about two hours. The run is also found in Table I as Run 5.

TABLE I

Hydrogenation of Furan Concentrate

| Run No. | Pre-Treatment of Furan Concentrate | Sulfur Content of Pre-Treated Concentrate | Catalyst Loading (Wt. % Feed) | Hydrogenation Temp., ° F | Hydrogenation Rate PSI/Min./g Ni |
|---|---|---|---|---|---|
| 1 | Distilled, overhead from IBP to 37° C (98.6° F) | 193 ppm | 0.5 | 260 | 2.5 |
| 2 | Distilled, overhead from IBP to 37° C (98.6° F) | 193 ppm | 5 | 270 | 17 |
| 3 | ZnO-Treated but not distilled | 59 ppm | 0.5 | 270 | V. slow |
| 4 | ZnO-Treated, then distilled, from IBP to 37° C (98.6° F) | 3 ppm | 0.5 | 260 | 70 |
| 5 | Distilled, overhead from 81.5 to 84° F. then ZnO-treated | 1 ppm | 0.5 | 250 | 140 |

EXAMPLE III

A nickel arsenide/alumina catalyst was prepared by impregnating 86.4 g of a 10–40 mesh granular catalytic grade gamma-alumina with an impregnating solution prepared by dissolving 42.6 g of $Ni(NO_3)_2.6H_2O$, and 8.9 g of $H_3AsO_4$ in 70 ml water. Essentially all the impregnating liquid was soaked by the alumina in three soaking operations with drying of the catalyst between the soakings. The impregnated alumina was then calcined at 900° F in a stream of air for 3 hours. It was then heated in a flow of hydrogen at 1000° F for 5 hours, then cooled to room temperature in flowing hydrogen.

The resulting catalyst was found to contain 8.9 weight percent nickel and 4.6 weight percent arsenic. Thus, the empirical formula of the nickel arsenide on the alumina can be represented as $NiAs_{0.41}$.

EXAMPLE IV

A furan concentrate, derived from by by-products of an oxidative dehydrogenation process for the conversion of butenes to butadiene, was subjected to the distillation and to the zinc oxide treatment of the present invention. It was then selectively hydrogenated by contact with hydrogen in the presence of the catalyst of the preceding Example III. The furan concentrate was passed through a fixed catalyst bed reactor at 200 psig, 280° F, 3–5 LHSV, and at a hydrogen:organic mole ratio of 0.63–0.84. The results of the hydrogenation are shown in Table II below.

TABLE II

| | Hydrogenation of Olefins and Diolefins in Furan Concentrate | |
|---|---|---|
| Component | Hydrogenation Feedstock | Hydrotreated Product |
| n-Butane | ND[1] | 0.58 |
| i-Pentane | ND | 0.88 |
| n-Pentane | ND | 1.23 |
| trans-Pentene-2 | 0.44 | 0.02 |
| cis-Pentene-2 | 0.83 | ND |
| 2-Methylbutene-2 | 0.24 | 0.14 |
| Isoprene | 1.58 | ND |
| 2-Butyne | 1.57 | ND |
| trans-Pentadiene | 0.56 | ND |
| cis-Pentadiene | 0.07 | ND |

TABLE II-continued

|  | Hydrogenation of Olefins and Diolefins in Furan Concentrate | |
|---|---|---|
| Component | Hydrogenation Feedstock | Hydrotreated Product |
| Cyclopentane | ND | 0.21 |
| Cyclopentadiene | ND[(2)] | ND |
| Furan | 94.68 | 92.76 |
| Tetrahydrofuran | ND | 4.05 |
| n-Butyl alcohol | ND | 0.11 |

[(1)]ND = not detected.
[(2)]A small amount of cyclopentadiene was believed present although the analytical method used could not detect it.

The data in Table II above show that an improved furan concentrate, which is essentially free of olefinic, acetylenic, and diolefinic contaminants, can be prepared by using a selective hydrogenation catalyst. With minimal losses of furan to tetrahydrofuran and n-butyl alcohol, unsaturates such as cis-pentene-2, isoprene, 2-butyne, trans-pentadiene, cis-pentadiene, and cyclopentadiene were destroyed. Other olefins were substantially reduced.

EXAMPLE V

Runs were carried out using zinc oxide with and without treatment with a base to treat a sulfur-containing furan concentrate prior to hydrogenation. In one run, zinc oxide was impregnated with about 7 weight percent sodium hydroxide prior to contacting with the furan concentrate.

The results of the runs, with and without sodium hydroxide treatment of a commercial zinc oxide absorbent, are given below in Table III. It will be noted that it was possible to operate at twice the space velocity with the base treated zinc oxide and still improve absorbent capacity.

TABLE III

|  | Run 1 | Run 2 |
|---|---|---|
| Absorbent | Zinc oxide | Zinc oxide |
| Treatment (base) | None | 7% NaOH |
| Process Conditions: | | |
| $\pi$, psig | 200 | 200 |
| Temp., °F | 540 | 560 |
| WHSV | 1.2 | 2.4 |
| Capacity-Sulfur Content of Bed | 1.7 to 2.2% S | 3.4% S |

It will be observed from the above runs that the effectiveness of the zinc oxide absorbent used in desulfurizing the furan concentrate prior to hydrogenation of the furan concentrate is improved and the capacity of the bed to hold the sulfur is increased by impregnating the zinc oxide with sodium hydroxide.

We claim:

1. A process for the selective hydrogenation of unsaturated contaminants present in furan concentrates without substantial hydrogenation of the furan which comprises selectively hydrogenating unsaturated materials comprising acetylenes, olefins, and diolefins present in furan distillate concentrates having an end boiling point less than about 80° F by contacting said concentrate and hydrogen in a molar ratio of hydrogen to feed of from about 0.1:1 to about 5:1 with a metal arsenide catalyst having the formula $MeAs_x$ wherein Me represents nickel, cobalt, or iron, and $x$ is a number which corresponds to the amount of arsenic which is in the range of 0.1–0.5 under hydrogenation conditions including a temperature in the range of about 75°–750° F and a pressure ranging from 0 to about 1,000 psig sufficient to convert said unsaturated materials to paraffins but insufficient to convert significant amounts of the furan to tetrahydrofuran to produce a paraffin-diluted furan concentrate.

2. A process according to claim 1 wherein said contacting is effected at a temperature in the range 150°–500° F and a feed rate in the range of 0.1–10 LHSV.

3. A process according to claim 1 wherein the metal arsenide catalyst is nickel arsenide supported on alumina and the furan concentrate is obtained from the effluent of an oxidative dehydrogenation process for the conversion of butenes to butadiene.

4. A process according to claim 1 wherein said furan concentrate is contacted with zinc oxide prior to hydrogenation to convert deleterious contaminants present in said concentrate to innocuous materials and thereby extend the life of the metal arsenide hydrogenation catalyst.

5. A process according to claim 1 wherein said furan concentrate is separated into a fraction boiling above about 80° C and a fraction boiling below about 80° C and further within the fraction boiling below about 80° C is contacted with zinc oxide prior to hydrogenation.

6. A process according to claim 5 wherein hydrogen is added to the furan concentrate prior to contacting with zinc oxide.

7. A process according to claim 1 wherein said furan concentrate is first subjected to distillation to remove overhead a fraction boiling below about 80° C which fraction is then contacted with zinc oxide in the presence of added hydrogen prior to hydrogenation.

8. A process according to claim 1 wherein said furan concentrate is obtained from the effluent of an oxidative dehydrogenation process and the concentrate is subjected to distillation to remove overhead materials boiling below about 80° C and then contacted with zinc oxide in the presence of added hydrogen before being passed to hydrogenation.

9. A process according to claim 1 for extending the life of hydrogenation catalysts and improving the hydrogenatability of furan concentrates to produce high purity furan products which comprises contacting a furan concentrate containing deleterious unsaturated hydrocarbon contaminants and sulfur compounds, but which is substantially free of high boiling materials, prior to hydrogenation, with zinc oxide at a temperature ranging from about 550° to about 850° F for a finite period of time sufficient to render innocuous compounds present in said concentrate which tend to inactivate hydrogenation catalysts, and hydrogenating said concentrate substantially free of catalyst inactivating materials by contacting with a metal arsenide hydrogenation catalyst and hydrogen under hydrogenation conditions sufficient to hydrogenate said unsaturated hydrocarbons to paraffinic materials but insufficient to convert significant amounts of the furan to tetrahydrofuran, and recovering a paraffin-diluted furan concentrate as product.

10. A process according to claim 4 wherein the zinc oxide has been treated with a base prior to contacting with the furan concentrate.

11. A process according to claim 10 wherein the base is sodium hydroxide and the amount of base added to the zinc oxide is in the range of 1 to 10 weight percent.

* * * * *